(12) United States Patent
Edin

(10) Patent No.: US 7,143,625 B2
(45) Date of Patent: Dec. 5, 2006

(54) STENT CRIMPER

(75) Inventor: Mark Edin, Minneapolis, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 158 days.

(21) Appl. No.: 10/826,196

(22) Filed: Apr. 16, 2004

(65) Prior Publication Data

US 2005/0234537 A1   Oct. 20, 2005

(51) Int. Cl.
*B21D 39/00* (2006.01)

(52) U.S. Cl. .................. 72/402; 72/416; 29/237; 29/283.5

(58) Field of Classification Search .......... 72/402, 72/416; 29/237, 282, 283.5
See application file for complete search history.

(56) References Cited

U.S. PATENT DOCUMENTS

| | | | |
|---|---|---|---|
| 565,257 A | 8/1896 | Boyd | |
| 758,195 A | 4/1904 | Schweinart et al. | |
| 1,665,915 A | 4/1928 | Ekman | |
| 1,889,795 A | 12/1932 | Smith et al. | |
| 2,292,421 A | 8/1942 | Wolf | 29/88.2 |
| 2,409,549 A * | 10/1946 | Djidics | 86/40 |
| 2,751,077 A | 6/1956 | Latin et al. | 207/4 |
| 2,887,222 A | 5/1959 | Latin et al. | 207/4 |
| 2,986,192 A | 5/1961 | Macleod | 153/1 |
| 3,416,352 A | 12/1968 | Ribback | 72/402 |
| 3,664,213 A | 5/1972 | Anati | 81/91 R |
| 3,695,087 A | 10/1972 | Tuberman | 72/402 |
| 3,731,518 A | 5/1973 | Blocher | 72/402 |
| 3,919,877 A * | 11/1975 | Netta | 72/456 |
| 4,304,116 A * | 12/1981 | Velarde | 72/383 |
| 4,337,635 A * | 7/1982 | Martin et al. | 72/409.09 |
| 4,434,645 A | 3/1984 | Svercl et al. | 72/402 |
| 4,567,650 A | 2/1986 | Balyasny et al. | 29/822 |
| 4,578,982 A | 4/1986 | Schrock | 72/402 |
| 4,604,890 A * | 8/1986 | Martin | 72/453.16 |
| 4,614,107 A * | 9/1986 | Norin | 72/402 |
| 4,854,031 A | 8/1989 | Eisenzimmer | 29/508 |
| 4,942,756 A | 7/1990 | Charzewski | 72/399 |
| 5,026,377 A | 6/1991 | Burton et al. | 606/108 |
| 5,138,864 A * | 8/1992 | Tarpill | 72/409.12 |
| 5,183,085 A | 2/1993 | Timmermans | 140/89 |

(Continued)

FOREIGN PATENT DOCUMENTS

WO    WO 02/11646 A1 *   2/2002

OTHER PUBLICATIONS

U.S. Appl. No. 10/788,088, filed Feb. 26, 2004, Weber et al.

*Primary Examiner*—Daniel C. Crane
(74) *Attorney, Agent, or Firm*—Vidas, Arrett & Steinkraus, P.A.

(57) ABSTRACT

An apparatus for reducing the size of a medical device, the apparatus including at least one independently operable discrete section which can reduce the diameter of the medical device, the independently operable discrete section including a plurality of coupled movable blades arranged to form an aperture whose size may be varied, the blades movable so as to allow the aperture to be sized to contain a medical device and to alter the size of the aperture. The blades may be curved and/or overlapping. Each blade may be pivotally connected to a first member or mount and slidably engaged with a second member or collar. The size of the aperture may be adjusted by rotating the collar relative to the mount.

35 Claims, 13 Drawing Sheets

U.S. PATENT DOCUMENTS

| | | | |
|---|---|---|---|
| 5,243,846 A | 9/1993 | Davis et al. | 72/402 |
| 5,261,263 A | 11/1993 | Whitesell | 72/410 |
| 5,381,686 A | 1/1995 | Thorup | 72/453.06 |
| 5,437,083 A | 8/1995 | Williams et al. | 29/235 |
| 5,509,184 A | 4/1996 | Herrero | 29/252 |
| 5,546,646 A | 8/1996 | Williams et al. | 29/407.08 |
| 5,626,604 A | 5/1997 | Cottone, Jr. | 606/198 |
| 5,630,830 A | 5/1997 | Verbeek | 606/198 |
| 5,672,169 A | 9/1997 | Verbeek | 606/1 |
| 5,692,294 A | 12/1997 | Casey | 29/753 |
| 5,715,723 A | 2/1998 | Owens | 72/402 |
| 5,725,519 A | 3/1998 | Penner et al. | 606/1 |
| 5,738,674 A | 4/1998 | Williams et al. | 606/1 |
| 5,746,764 A | 5/1998 | Green et al. | 606/194 |
| 5,768,935 A * | 6/1998 | Owens | 72/416 |
| 5,810,873 A | 9/1998 | Morales | 606/198 |
| 5,836,952 A | 11/1998 | Davis et al. | 606/108 |
| 5,860,966 A | 1/1999 | Tower | 606/1 |
| 5,893,852 A | 4/1999 | Morales | 606/108 |
| 5,911,752 A | 6/1999 | Dustrude et al. | 623/1 |
| 5,920,975 A | 7/1999 | Morales | 29/282 |
| 5,931,851 A | 8/1999 | Morales | 606/194 |
| 5,951,540 A | 9/1999 | Verbeek | 606/1 |
| 5,974,652 A | 11/1999 | Kimes et al. | 29/516 |
| 5,992,000 A | 11/1999 | Humphrey et al. | 29/516 |
| 6,009,614 A | 1/2000 | Morales | 29/516 |
| 6,018,857 A | 2/2000 | Duffy et al. | 29/407.01 |
| 6,051,002 A | 4/2000 | Morales | 606/108 |
| 6,063,102 A | 5/2000 | Morales | 606/198 |
| 6,074,381 A | 6/2000 | Dinh et al. | 606/1 |
| 6,082,990 A | 7/2000 | Jackson et al. | 425/517 |
| 6,108,886 A | 8/2000 | Kimes et al. | 29/280 |
| 6,125,523 A | 10/2000 | Brown et al. | 29/516 |
| 6,141,855 A | 11/2000 | Morales | 29/516 |
| 6,167,605 B1 | 1/2001 | Morales | 29/282 |
| 6,240,615 B1 | 6/2001 | Kimes et al. | 29/516 |
| 6,309,383 B1 | 10/2001 | Campbell et al. | 606/1 |
| 6,352,547 B1 | 3/2002 | Brown et al. | 606/198 |
| 6,360,577 B1 | 3/2002 | Austin | 72/402 |
| 6,387,117 B1 * | 5/2002 | Arnold et al. | 623/1.1 |
| 6,481,262 B1 | 11/2002 | Ching et al. | 72/416 |
| 6,484,553 B1 * | 11/2002 | Devers | 72/402 |
| 6,568,235 B1 | 5/2003 | Kokish | 72/402 |
| 6,629,350 B1 | 10/2003 | Motsenbocker | 29/283.5 |
| 6,651,478 B1 | 11/2003 | Kokish | 72/402 |
| 6,769,161 B1 * | 8/2004 | Brown et al. | 29/234 |
| 6,925,847 B1 * | 8/2005 | Motsenbocker | 72/402 |
| 2002/0035774 A1 | 3/2002 | Austin | 29/516 |
| 2002/0128996 A1 | 9/2002 | Reed | 707/1 |
| 2002/0138966 A1 | 10/2002 | Motsenbocker | 29/516 |
| 2002/0161426 A1 | 10/2002 | Iancea | 623/1.11 |
| 2003/0056360 A1 | 3/2003 | Brown et al. | 29/516 |
| 2003/0150250 A1 | 8/2003 | Shortt | 72/235 |
| 2003/0192164 A1 | 10/2003 | Austin | 29/505 |

* cited by examiner

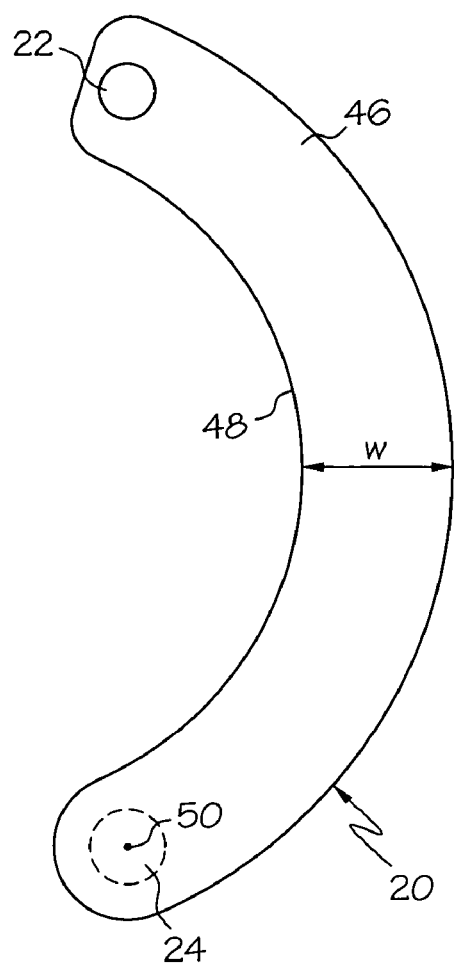
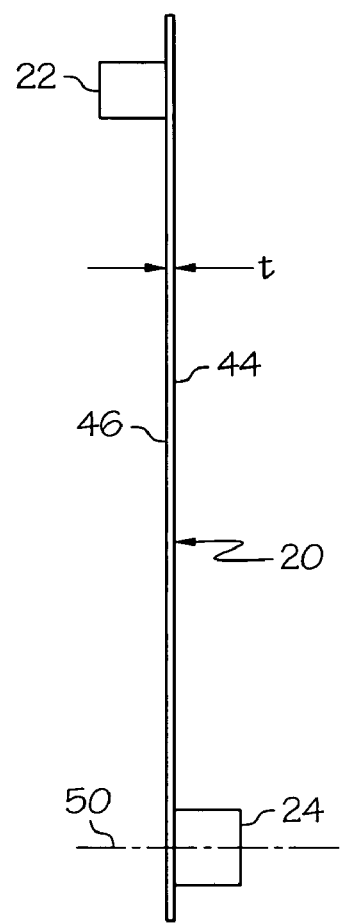
FIG. 3
FIG. 4

STENT CRIMPER

BACKGROUND OF THE INVENTION

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are available in both self-expanding and inflation or balloon expandable configurations. Inflation expandable stents are well known and widely available in a variety of designs and configurations. Both self-expanding and inflation expandable stents are typically crimped to their reduced configuration after being disposed about a delivery catheter or about the balloon of a delivery catheter. They are maneuvered to the deployment site and expanded to the vessel diameter either by fluid inflation of a balloon positioned between the stent and the delivery catheter, or upon release of the self-expanding stent from its crimped state, typically from a retaining sleeve.

Devices for reducing the diameter of stents are generally known, such as described in U.S. Pat. No. 6,360,577 to Austin, the entire disclosure of which is incorporated herein by reference.

Self-expanding stents offer some unique challenges when being loaded on a catheter in part because they have a tendency to open of their own volition at ambient conditions. Thus, it is common practice when loading a self-expanding stent onto a catheter, to constrain only one half of the length of a strut at one time. This is more time and labor intensive because it requires reducing the diameter of the stent a little bit of the stent at a time.

There remains a need in the art for a crimping device that provides more flexibility during the crimping process.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

It would be desirable to produce a device capable of crimping a stent while minimizing the distortion of, and scoring and marking of the stent due to the crimping. The present invention is directed, in at least one aspect, to that end.

The present invention is related to the crimping or otherwise reducing in size of inflation expandable stents, self-expanding stents and other expandable medical devices. The invention is also related to loading or otherwise placing an inward force on a medical device. For the purpose of this disclosure, it is understood that the term "medical device" includes stents, stent-grafts, grafts and vena cava filters. It is also understood that the term "crimping" refers to a reduction in size or profile of a medical device. It is further understood that the invention contemplates crimping a medical device either directly to a catheter tube or to a catheter balloon which is disposed about a catheter tube. When reference is made to crimping a medical device about a catheter, a balloon may be situated between the medical device and the catheter tube or the medical device may be disposed directly about a region of a catheter tube. The invention also contemplates crimping a medical device such as a stent, in the absence of a catheter.

The apparatus according to the present invention is designed for applying inward forces to the medical device. In some embodiments, the apparatus includes at least one independently operable crimping section, the section having a housing which includes a movable ring and a stationary ring, the stationary ring retaining at least three coupled, independently movable blades. The blades may be disposed about a reference circle to form an aperture whose size may be varied. The blades are movable so as to allow the aperture to be sized to contain a medical device and to alter the size of the aperture. The blades may be actuated by the relative orientation of the stationary ring with respect to the movable ring, which is rotatable with respect to the stationary ring. The stationary ring may engage and retain the blades about the reference circle at uniform distances from one another.

Each blade may be pivotally attached to the stationary member at a pivot point. Each blade may be slidably engaged with the rotatable member. In some embodiments, each blade may include a pivot pin and a sliding pin. The pivot pin for each blade may be received by a respective aperture in the stationary member. The sliding pin for each blade may be slidably engaged within a respective slot in the rotatable member. As the rotatable member is rotated with respect to the stationary member, each blade may pivot about its pivot point, thereby changing the size of the aperture formed by the blades. As the rotatable member is rotated with respect to the stationary member, the sliding pin of each blade may translocate within its respective slot in the rotatable member.

Each crimping section may have at least 2 blades and may have any number of additional blades. Desirably 3 to 32 blades may be used. More desirably about 4 to 16, and even more desirably about 6 to 8 blades may be used. The blades may be disposed about a reference circle to form an aperture of continuously variable size. The number of blades may vary depending on the blade width and the area to be filled relative to the blade width.

Suitably, the blades are overlapping, although this does not preclude the case where they do not overlap one another.

In one embodiment, the blades have a curved edge, wherein the area of the blades which comes into contact with the medical device which is being reduced in size, is curved.

The blades of the device may be any size suitable for crimping or otherwise loading a medical device. In some embodiments, the thickness of the blades, and thus the length of the aperture or chamber formed by the blades, may be greater than the length of a medical device to be crimped. In some embodiments, each blade may be very thin, having a thickness of about 0.001" to about 0.003" or about 0.025 mm to about 0.075 mm. The width of each blade may be about 0.050" to about 0.150" (about 1.3 mm to about 3.8 mm), or about 1 mm to about 4 mm. In one embodiment the blades may have a thickness of about 0.002" or about 0.05 mm. The blades have a width of about 0.120" or about 3 mm.

If the medical device which is being reduced in size is a stent, it is desirable in some embodiments for the thickness of each blade to be equal to or less than the length of the strut of a stent, or less than the length component of a ring member or serpentine band included in the stent. Thus, in some embodiments, it is desirable that the apparatus according to the invention include a plurality of crimping sections. Desirably, two or more sections of the crimping device may contact each strut of a stent being crimped. The length of the aperture formed by each crimping section may be less than the length of a strut. In this fashion, the crimping device may be designed based on the design of the stent and its strut length.

The blades may be formed from polymeric materials, ceramic, and metals. Examples of suitable metals include, but are not limited to, stainless steel, tempered blue steel, blackened corrosion resistant spring steel, and so forth.

The blades may optionally include a coating. In one embodiment, the blades include a coating which reduces the coefficient of friction between the blade and the surface of the medical device to which it comes into contact. Examples of suitable coatings of this nature include, for example, coatings based on fluoropolymers such as polytetrafluoroethylene. Such coatings can be advantageous when the medical device has a coating, such as a coating including a therapeutic drug, in order to reduce the damage to the coating on the surface of the medical device.

If the apparatus has a plurality of independently operable discrete crimping sections, each crimping section may be independently actuated and controlled such that the blades from one crimping section may or may not simultaneously move with the blades from another crimping section. Thus, different parts of the medical device may be crimped to the same or different diameters at the same or different times. The crimping sections are suitably configured and arranged such that the apertures of each crimping section may be centered about the same axis, which may comprise a central longitudinal axis of the apparatus. The collective apertures arranged adjacent to one another may comprise a substantially continuous aperture or chamber. A medical device such as a stent, is placed into the variable aperture of each crimping section, and the blades from each crimping section are simultaneously moved inward to apply a radial inward force to the medical device.

In another aspect, the present invention relates to an apparatus for reducing the size of a medical device, the apparatus including at least one independently operable discrete section which can reduce the diameter of the medical device. The independently operable discrete section includes a plurality of coupled movable blades disposed about a reference to form an aperture whose size may be varied, the blades movable so as to allow the aperture to be sized to contain a medical device and to alter the size of the aperture. The blades have a contact area with said medical device which is curved.

The present invention can be advantageously used for reducing the size of stents formed from a shape memory material such as Nitinol and the like, which are capable of self-expansion. The stent may be plastically deformed in the martensitic state for loading into a constraining delivery system.

These and other embodiments which characterize the invention are pointed out with particularity in the claims annexed hereto and forming a part hereof. However, for a better understanding of the invention, its advantages and objectives obtained by its use, reference should be made to the drawings, which form a further part hereof, and the accompanying descriptive matter, in which there are illustrated and described various embodiments of the invention.

BRIEF DESCRIPTION OF THE DRAWINGS

FIG. 3 is a side view of an embodiment of a blade.

FIG. 4 is another side view of an embodiment of a blade.

DETAILED DESCRIPTIONS OF THE PREFERRED EMBODIMENTS

Figure 1:
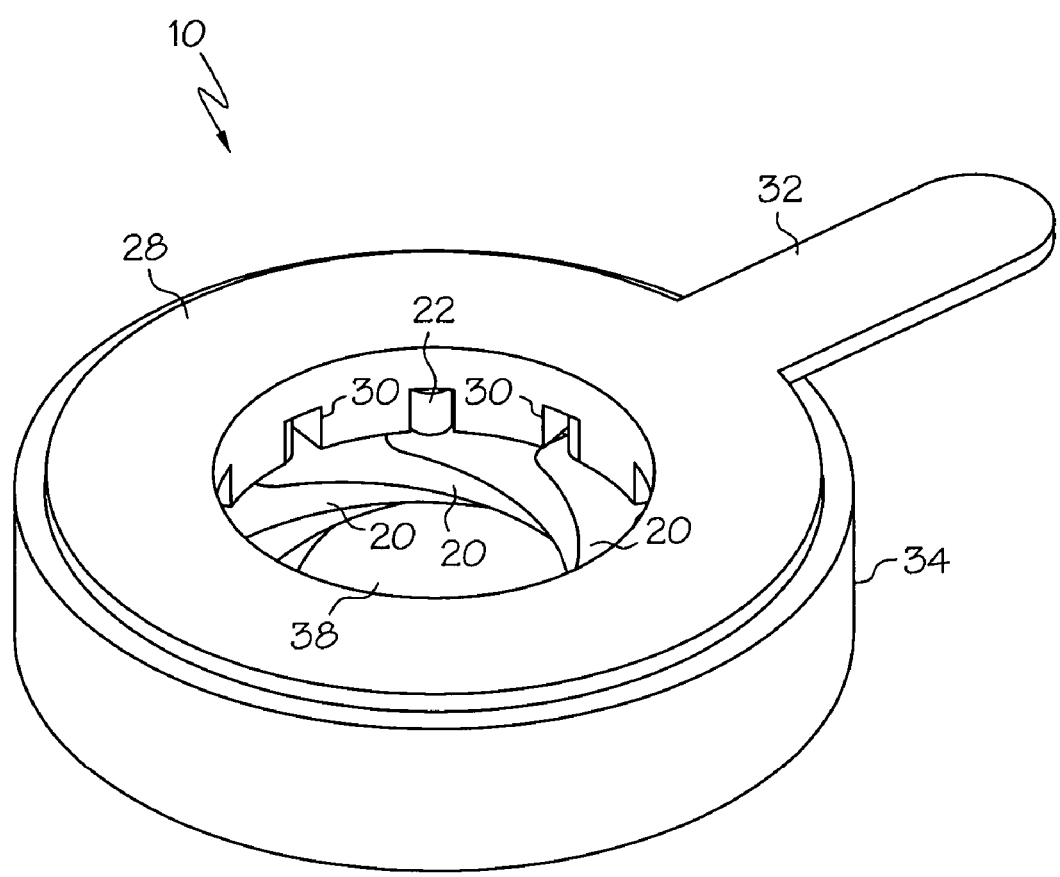
FIG. 1 is a perspective view of one embodiment of the invention.

While this invention may be embodied in many different forms, there are described in detail herein by way of illustration, specific embodiments of the invention. This description is an exemplification of the principles of the invention and is not intended to limit the invention to the particular embodiments illustrated.

The term crimping, as used herein, refers to a reduction in size or profile of the medical device.

For the purposes of this disclosure, like reference numerals in the figures shall refer to like features unless otherwise indicated.

Figure 2:
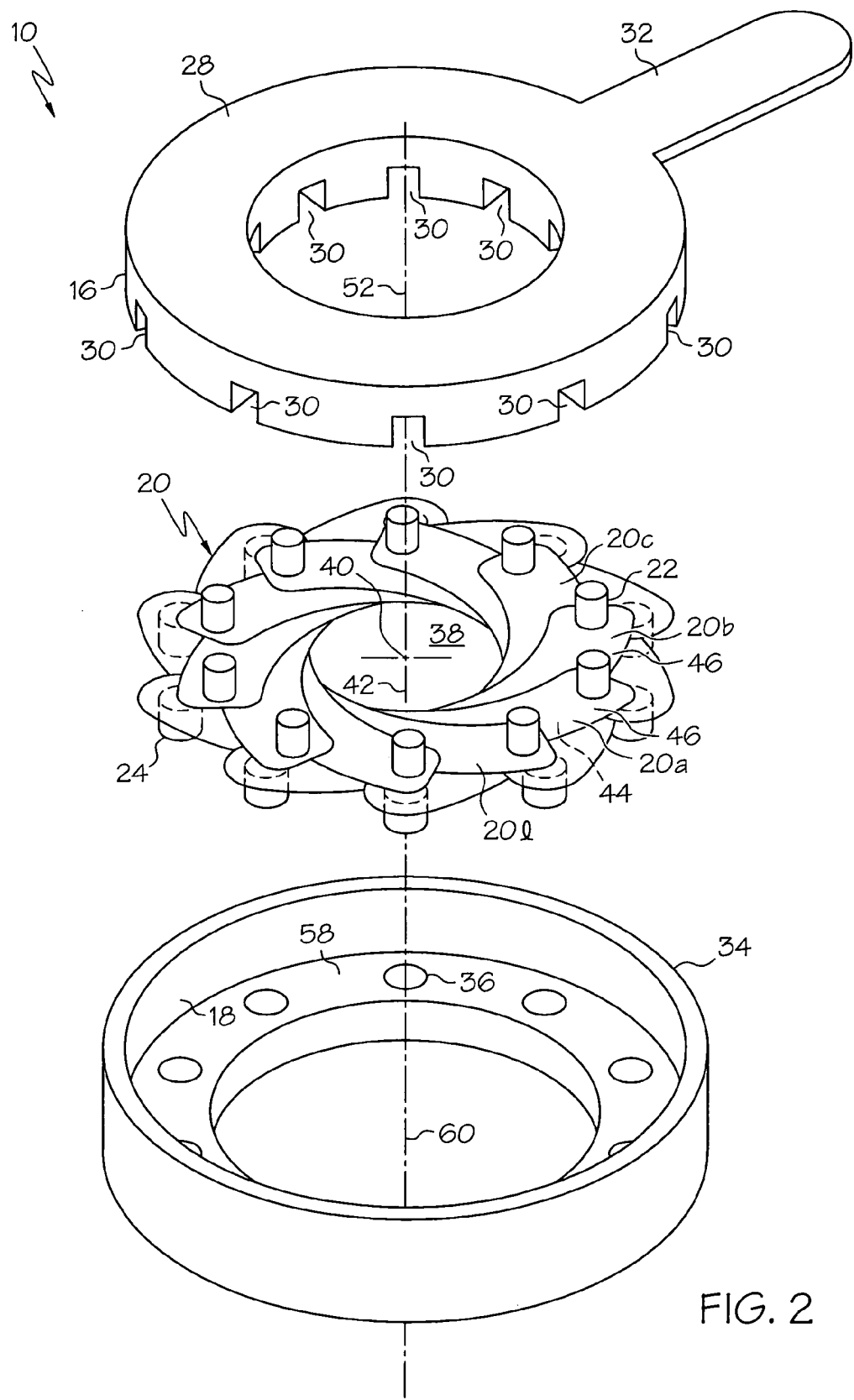
FIG. 2 is an exploded view of one embodiment of the invention.

FIGS. 1 and 2 show an embodiment of a device 10 which may be used to shape an article, such as a medical device. The device 10 may comprise a stationary mount 34, a rotatable guide member or collar 28 and a plurality of blades 20. The blades 20 may be arranged to form an aperture 38 whose size may be varied. The rotatable collar 28 may be rotatable with respect to the stationary mount 34. The size of the aperture 38 may be adjusted by rotating the rotatable collar 28 with respect to the stationary mount 34.

FIGS. 3 and 4 show details of one embodiment of a blade 20. A blade 20 may have a first side 44, a second side 46 and a contacting surface 48. The contacting surface 48 may bound a portion of an aperture formed by a plurality of blades 20. In some embodiments, the face of a contacting surface 48 may be orthogonal to the first side 44 and/or the second side 46. A contacting surface 48 may have curvature along the length of the blade 20.

When the device 10 is assembled, each blade 20 may be arranged to pivot about a pivot point or pivot axis 50. A first pin or pivot pin 24 may extend from the first side 44 of the blade 20. Desirably, the pivot pin 24 is centered on the pivot axis 50.

Each blade 20 may further include a second pin or sliding pin 22 which may extend from the second side 46 of the blade 20. A sliding pin 22 may comprise a portion of one embodiment of a mechanism allowing sliding engagement between a blade 20 and the rotatable collar 28.

Figure 5:
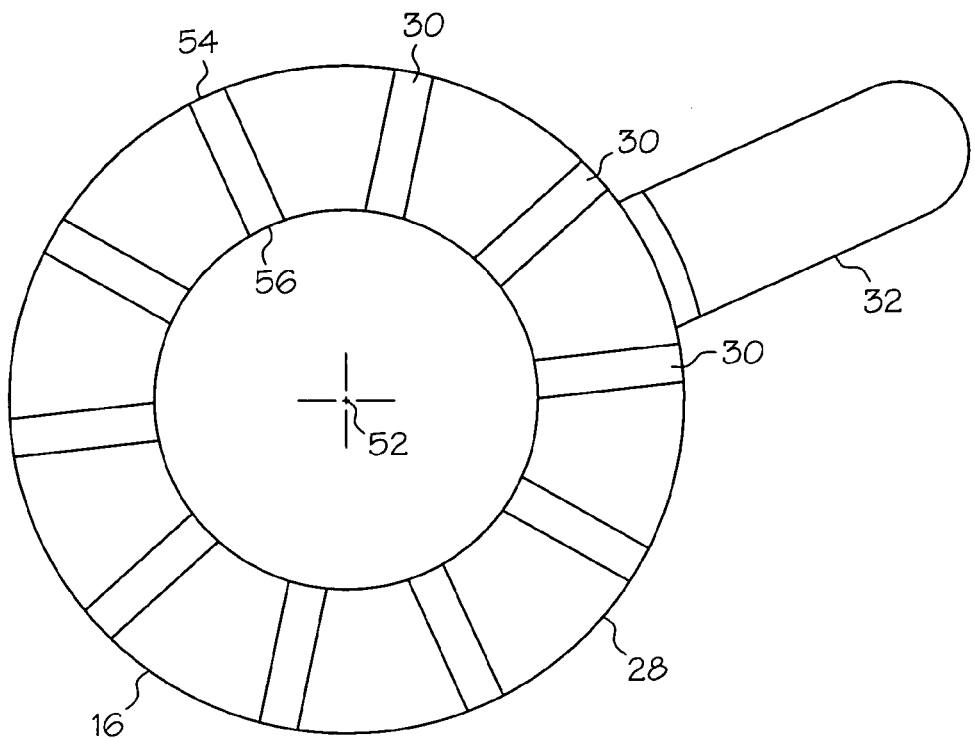
FIG. 5 is a view of the underside of an embodiment of a collar.

FIG. 5 shows the underside of one embodiment of a rotatable collar 28, which may have a generally annular shape centered about a collar axis 52. The rotatable collar 28 may have an outer wall 16 and may include a plurality of slots 30. In some embodiments, one slot 30 is provided for each blade 20 of the device 10. Each slot may have a first end 54 and a second end 56. The slots 30 may be radially oriented and may be sized to receive a sliding pin 22 of a blade 20. In some embodiments, a rotatable collar 28 may include an actuation handle or lever 32 for effecting rotation of the collar 28 with respect to the mount 34.

Referring again to FIGS. 1 and 2, the blades 20 may be arranged to form an aperture 38. The blades 20 may be arranged about a reference or zero point 40. The contacting surfaces 48 of the blades 20 may bound the aperture 38. The center of the aperture 38 may comprise the zero point 40. A portion of each blade 20 may meet at the zero point 40 when the aperture 38 is fully closed. A central longitudinal axis 42 of the aperture 38 may pass through the zero point 40.

Various embodiments of the device 10 may include two or more blades 20 arranged to form an aperture 38. Desirably, the number of blades may be between about 2 and 32, more desirably between about 4 and 16, and most desirably between about 6 and 10.

At least two of the blades 20 may be arranged to overlap one another in a direction parallel to the central longitudinal axis 42 of the aperture 38.

In some embodiments, the blades 20 may be arranged to form an iris diaphragm. The blades 20 may be arranged to "continuously overlap" as the blades 20 are traversed in a given direction about the zero point 40, such as in a clockwise or counterclockwise direction. For example, a portion of each blade 20 may be arranged to overlay a portion of the next blade as the blades 20 are traversed in a predetermined direction about the zero point 40. Referring to FIG. 2, a first blade 20a may be positioned to overlay a portion of a second blade 20b such that the first side or underside 44 of the first blade 20a contacts the second side or topside 46 of the second blade 20b. The second blade 20b may be arranged to overlay a portion of a third blade 20c such that the underside 44 of the second blade 20b contacts the topside 46 of the third blade 20c. The pattern may continue until the last blade 20l of the device is reached, wherein the last blade 20l may be arranged to overlay a portion of the first blade 20a such that the underside 44 of the last blade 20l contacts the topside 46 of the first blade 20a. Thus, the blades 20a–20l may continuously overlap one another as the blades 20 are traversed about the zero point 40 in a counterclockwise direction. In other words, each blade, for example blade 20a, may overlap a portion of a first adjacent blade 20b and may be overlapped by a portion of a second adjacent blade 20l. The overlap may be in a direction parallel to the central longitudinal axis 42 of the aperture 38. In some embodiments, non-contacting surfaces of adjacent blades 20, or surfaces other than contacting surfaces 48 of adjacent blades, may contact and overlap one another in a parallel to the central longitudinal axis 42 of the aperture 38. In some embodiments, a line parallel to the central longitudinal axis 42 of the aperture 38 may intersect at least two blades. In some embodiments, a line parallel to the central longitudinal axis 42 of the aperture 38 may intersect three blades, four blades, or five or more blades.

The stationary mount 34 may have a generally annular shape and a central axis 60, although any desired shape may be used. The stationary mount 34 may have a mount portion 58 and a wall portion 18. The wall portion 18 may have an annular shape and may extend from the mount portion 58 in a direction parallel to the axis 42 of the aperture 38.

Each blade 20 may be pivotally connected to the stationary mount 34. The mount portion 58 may include a plurality of pivot apertures 36. In some embodiments, one pivot aperture 36 may be provided for each blade 20. Each pivot aperture 36 may receive the pivot pin 24 of a blade. The center of a pivot aperture 36 may lie along the blade pivot axis 50 (see FIGS. 3 and 4) of the blade 20 to which the pivot aperture 36 is engaged.

Each blade may be 20 may be slidably engaged with the rotatable collar 28. For example, each blade 20 may include a sliding pin 22 which may be received by a slot 30 in the rotatable collar 28.

When the device 10 is assembled, the blades 20 may be received by the stationary mount 34, and the rotatable collar 28 may be positioned to overlay the blades 20 and be received by the stationary mount 34. The outer wall 16 of the rotatable collar 28 may be adjacent to and may abut an inner surface of the wall portion 18 of the stationary mount 34. The rotatable collar 28 may be rotatable with respect to the stationary mount 34, which may adjust the size of an aperture 38 formed by the blades 20.

The rotatable collar axis 52, stationary mount axis 60 and the central longitudinal axis 42 of the aperture 38 may all comprise a common line.

FIGS. 6–11 show the positioning of the blades 20 of an embodiment of the device 10 at various rotational orientations between the stationary mount 34 and the rotatable collar 28. The Figures illustrate how rotation of the rotatable collar 28 with respect to the stationary mount 34 may adjust the size of the aperture 38 formed by the blades 20.

Figure 6:
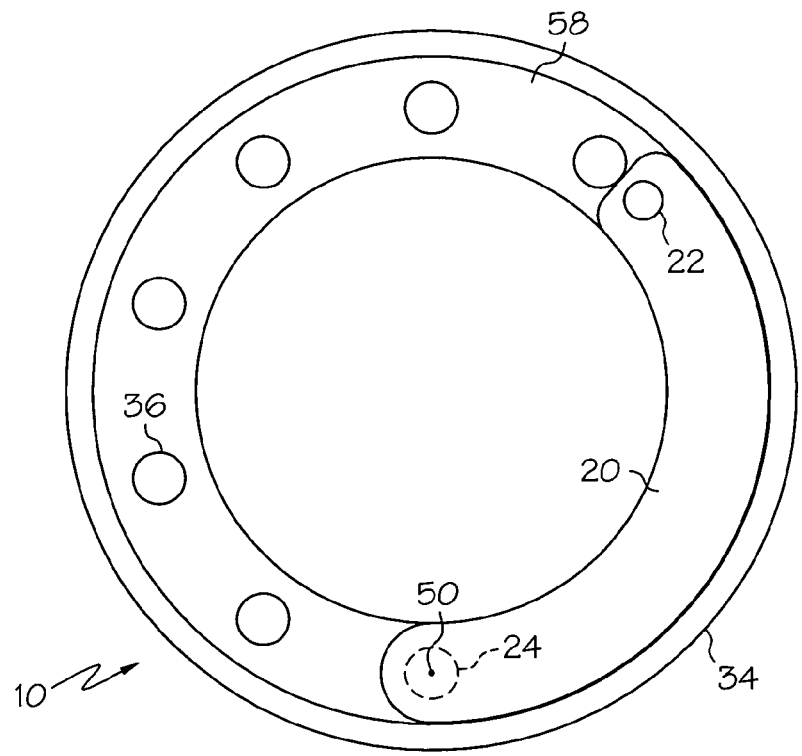
FIG. 6 shows an embodiment of a mount and a single blade.

FIG. 6 shows a stationary mount 34 and a blade 20 in a first position which may comprise a first end of a travel path that the blade 20 may traverse. The blade 20 may be pivotally attached to the mount 34, and may be arranged to pivot about the blade pivot axis 50.

Figure 7:
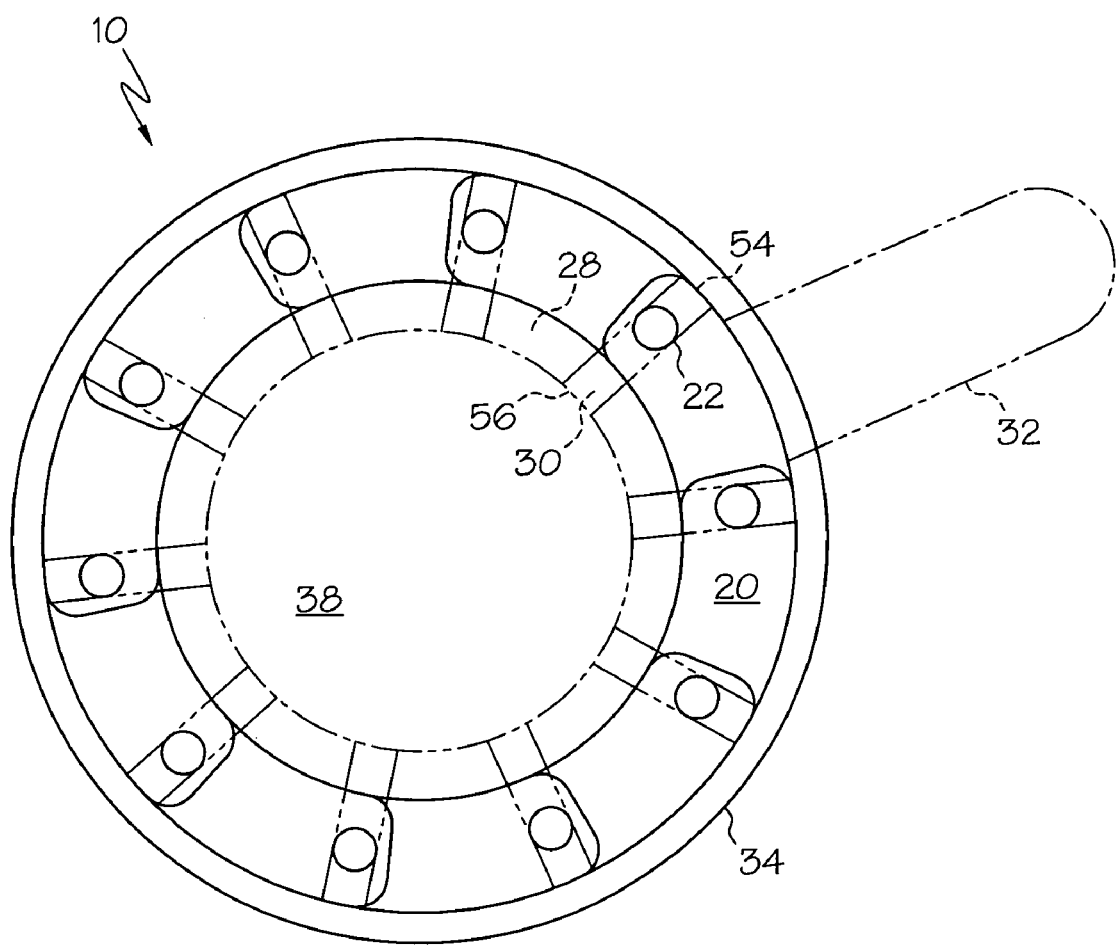
FIG. 7 shows an embodiment of the device wherein the aperture is fully open.

FIG. 7 shows an embodiment of the device 10 wherein a plurality of blades 20 are arranged to form an aperture 38, each blade being in a first position as depicted in FIG. 6 with respect to one blade. The aperture 38 may be fully open and may be at a maximum size. The blades 20 may be arranged in a continuously overlapping relationship as previously described herein.

A rotatable collar 28 is shown in phantom lines at a first rotational orientation with respect to the stationary mount 34. The sliding pin 22 of each blade 20 may be received within a respective slot 30 of the rotatable collar 28. Each sliding pin 22 may be slidably engaged with a respective slot 30. Each sliding pin 22 may be at a first end of a travel path that the sliding pin 22 may traverse as the rotatable collar 28 is rotated with respect to the stationary mount 34. At the rotational orientation depicted in FIG. 7, each sliding pin 22 may be in relative proximity to the first end 54 of its respective slot 30.

Figure 8:
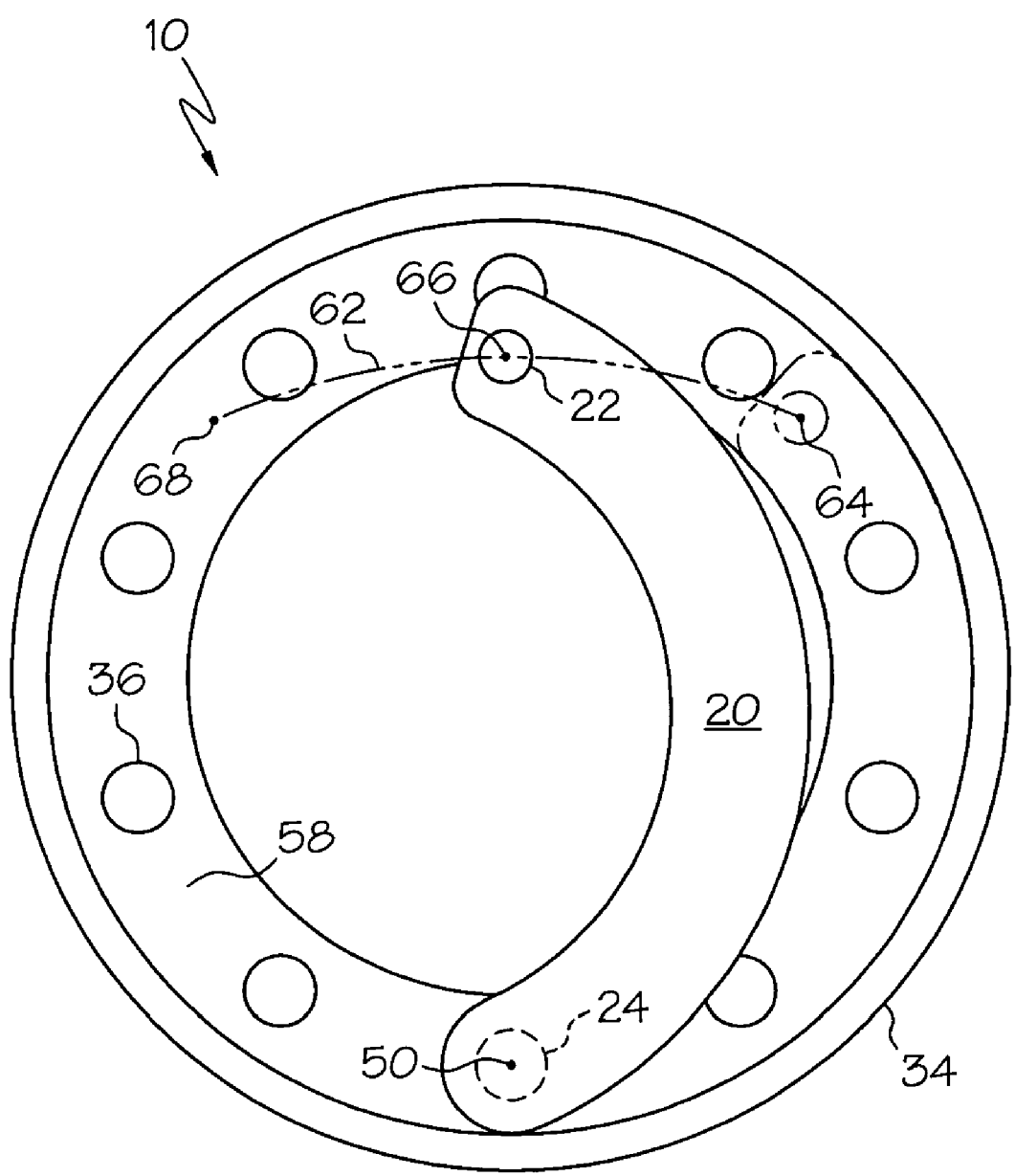
FIG. 8 shows an embodiment of a mount and a single blade in another position.

FIG. 8 shows a stationary mount 34 and a blade 20 in another position displaced from the first position shown in FIG. 6. A blade 20 in the first position is shown in hidden lines. The blade 20 may have traversed a portion of its travel path 62, and may have pivoted about the blade pivot axis 50.

As depicted, the travel path 62 comprises an arc about the pivot axis 50 of the blade 20. The center of the sliding pin 22 may traverse the travel path 62.

Figure 9:
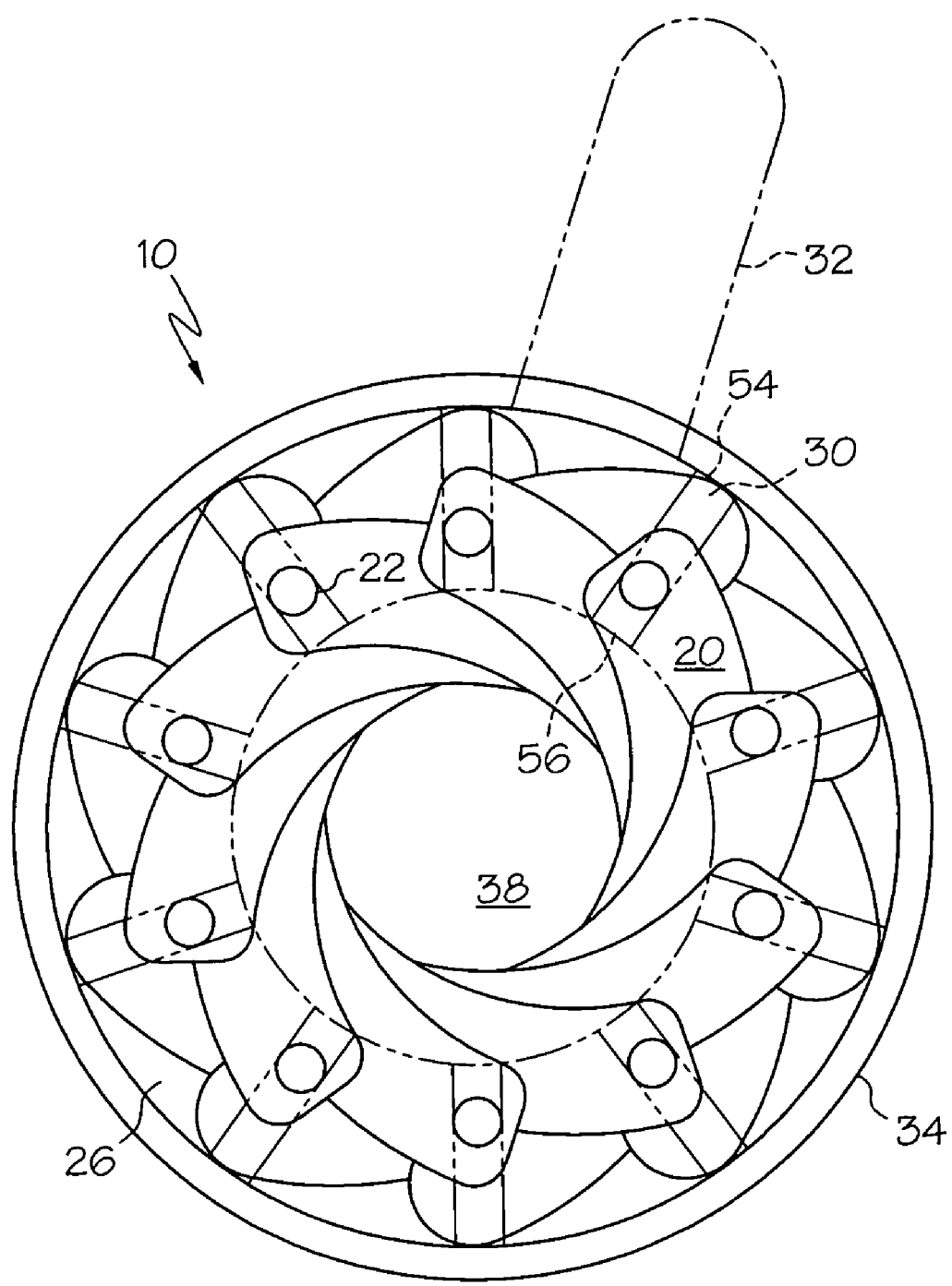
FIG. 9 shows an embodiment of the device wherein the aperture is partially open.

FIG. 9 shows an embodiment of the device 10 wherein a plurality of blades 20 are arranged to form an aperture 38, each blade being in a position midway along its travel path 62, as depicted in FIG. 8 with respect to one blade. The aperture 38 may be partially open and may have an intermediate size. A rotatable collar 28 is shown in phantom lines. The rotational orientation of the rotatable collar 28 with respect to the stationary mount 34 may be different from the rotational orientation depicted in FIG. 7, as indicated by the location of the actuation lever 32.

As the rotatable collar 28 rotates with respect to the mount 34, each slot 30 may displace and may bear against the sliding pin 22 of a respective blade 20, causing the blade 20 to pivot about its pivot axis 50. As the slot 30 displaces and the blade 20 pivots, the sliding pin 22 of the blade 20 may traverse a portion of the slot 30 in the lengthwise direction of the slot 30. The lengthwise direction of the slot 30 may be in a radial direction with respect to the aperture axis 42 (see FIG. 2).

As the rotational orientation of the rotatable collar 28 with respect to the stationary mount 34 changes and the size of the aperture 38 is changed from fully open to fully closed, or vice versa, each blade 20 may traverse an entire travel path 62 as shown in FIG. 8. As the blade 20 traverses the entire travel path 62, the sliding pin 22 of the blade may traverse a portion of a slot 30 along the length of the slot 30. As the blade 20 moves from a first end 62 of the travel path 62 to a midpoint 66 of the travel path 62, the sliding pin 22 may traverse the slot 30 in a first direction. As the blade moves from the midpoint 66 of the travel path 62 to a second end 68 of the travel path 62, the sliding pin 22 may reverse the direction of its sliding engagement with the slot 30 and may traverse the slot 30 in a second direction which may be opposite the first direction. For example, during the first half of movement of the blade 20 along its travel path 62, the sliding pin 22 may traverse the slot 30 in a radially inward direction. During the second half of movement of the blade 20 along its travel path 62, the sliding pin 22 may traverse the slot 30 in a radially outward direction. Thus, when the blade 20 is oriented at the midpoint of its travel path 62, the sliding pin 22 may be positioned at one end its traversal of the slot 30 and may be in relative proximity to the second end 56 of the slot 30 (see FIG. 9).

Figure 10:
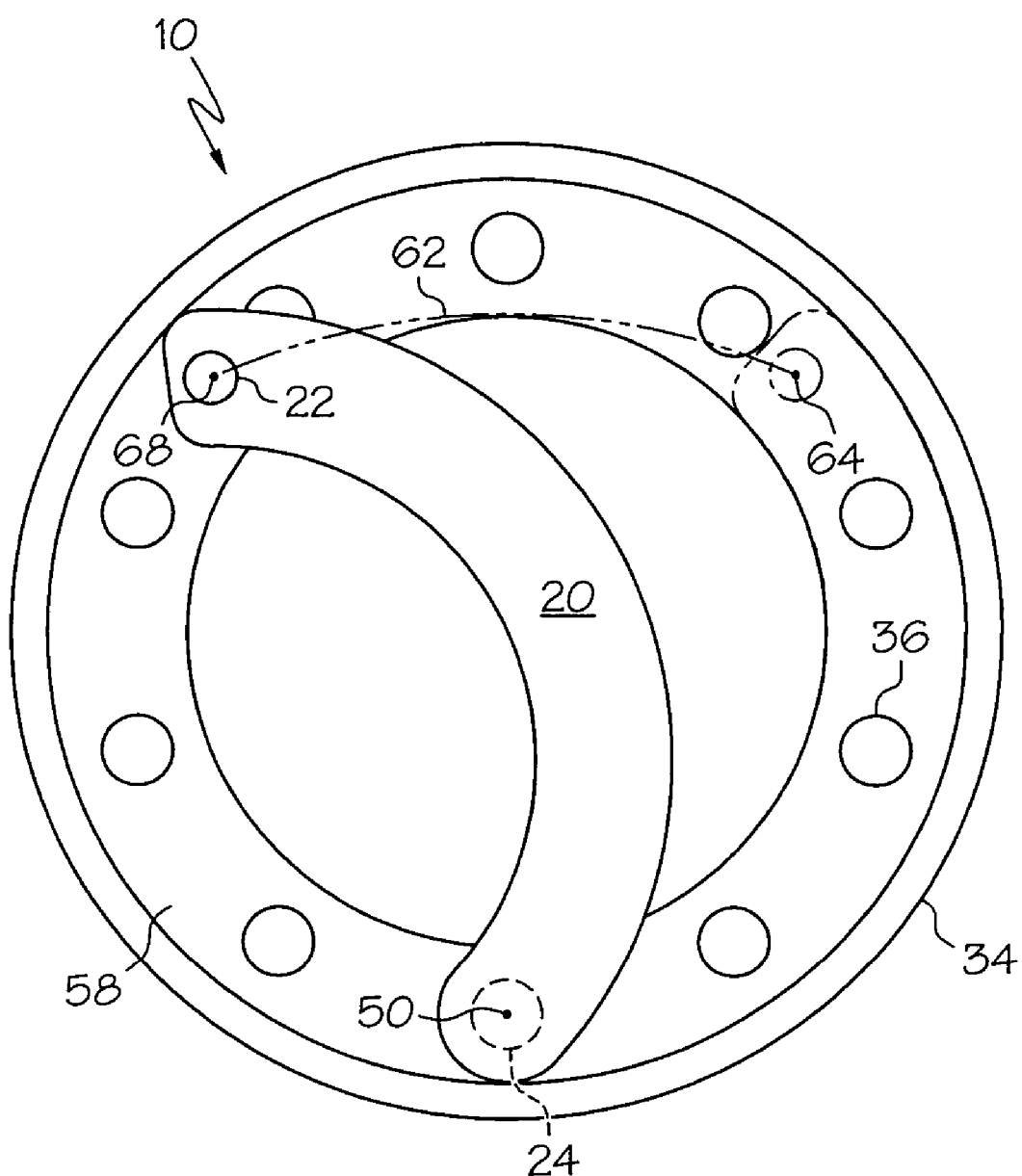
FIG. 10 shows an embodiment of a mount and a single blade in another position.

FIG. 10 shows a stationary mount 34 and a blade 20 in another position which may be at the second end 68 of the travel path 62. A blade 20 in the first position is also shown in hidden lines. The blade 20 may have traversed the entire travel path 62, pivoting about the blade pivot axis 50.

Figure 11:
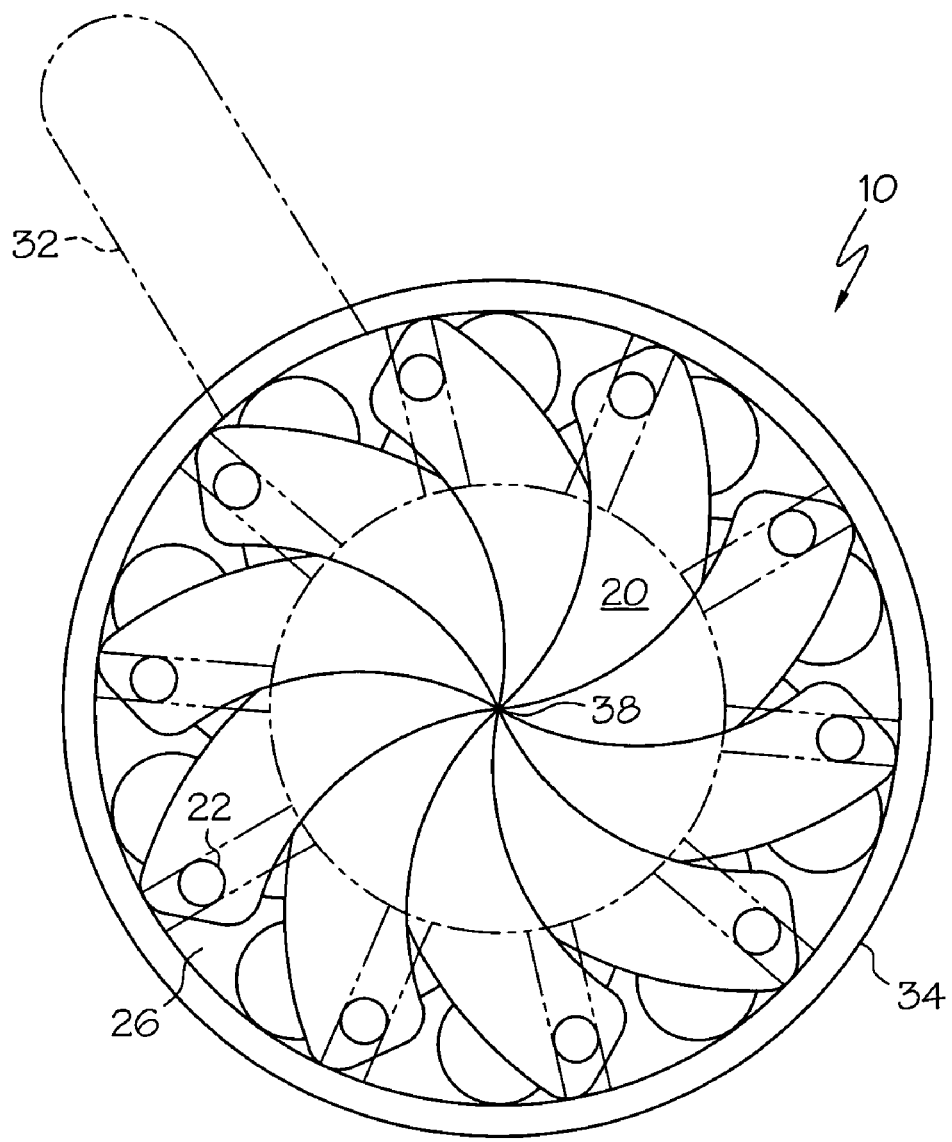
FIG. 11 shows an embodiment of the device wherein the aperture is closed.

FIG. 11 shows an embodiment of the device 10 wherein a plurality of blades 20 are arranged to form an aperture 38, each blade being positioned at a second end 68 of its travel path 62, as depicted in FIG. 10 with respect to one blade. The aperture 38 may be substantially closed or fully closed. A rotatable collar 28 is shown in phantom lines. The rotational orientation of the rotatable collar 28 with respect to the stationary mount 34 may be different from the rotational orientation depicted in FIGS. 7 and 9, as indicated by the location of the actuation lever 32.

The size of an aperture 38 may be continuously adjustable from fully open to fully closed by adjusting the rotational orientation of the rotatable collar 28 with respect to the mount 34.

Referring again to FIGS. 3 and 4, each blade 20 may have a thickness t in a direction parallel to the aperture axis 42 (FIG. 2) of the aperture 38 formed by a plurality of blades 20. The thickness t of the blades 20 may determine the length of the aperture 38. Generally, the length of the aperture 38 may be greater than the thickness t of individual blades 20 because of the continuously overlapping relationship of the blades 20 when arranged to form an aperture 38.

In some embodiments, the thickness t of each blade 20 may be the same as the thickness t of all of the other blades 20 of the device 10. Blades 20 may have any desired thickness t. In some embodiments, the thickness t of a blade may be relatively thin and may range from 0.005 inches to 0.001 inches or less, or from about 0.13 mm to about 0.025 mm or less. It is also within the scope of the invention to use thicker blades. In some embodiments, the thickness t of a blade may be 0.002 inches, or about 0.05 mm.

Figure 12:
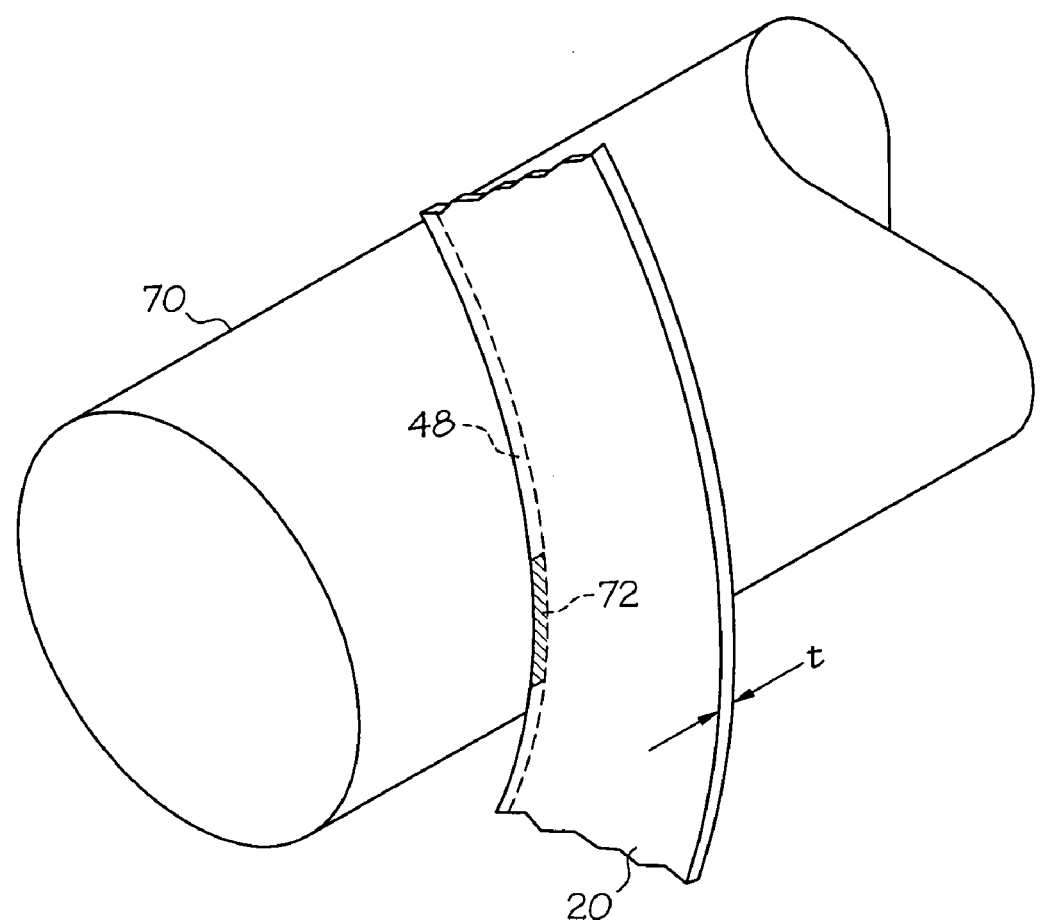
FIG. 12 shows a blade contacting an article, such as a medical device.

FIG. 12 shows a portion of the contacting surface 48 of a blade 20 contacting a portion of an article 70. The area of contact may comprise a contact area or contact patch 72. A relatively thin blade 20 may provide a relatively thin contact patch 72 where the contacting surface 48 of the blade 20 contacts and applies a load to the article. Thin blades 20 may be desirable when crimping certain articles, such as drug-coated stents, as a thin contact area may achieve a desired crimp with less marring of the coating than can be achieved using conventional crimpers having thicker blades.

Referring again to FIG. 3, each blade 20 may have a width measurement w which may be measured in a direction perpendicular to a portion of a contacting surface 48. As depicted in FIG. 3, a contacting surface 48 may have curvature along its length. A blade 20 having a curved contacting surface 48 may be dimensioned such that the width measurement w across the blade in a direction perpendicular to any portion of the contacting surface 48 may be constant. Blades 20 may have any suitable width w. In some embodiments, the width w may range from 0.15 inches to 0.05 inches, or about 3.8 mm to about 1.3 mm. In some embodiments, the width w of a blade may be 0.12 inches, or about 3 mm.

A blade 20 having a contacting surface 48 with curvature may provide for a longer contact patch 72 (see FIG. 12) than would be provided by a contacting surface 48 without curvature when using the device to crimp an article 70 having curvature. The increased length of the contact patch 72 may provide the patch 72 with a greater total amount of area, which may reduce the amount of stress placed on the portion of the article 70 within the area of the contact patch 72.

The blades 20 according to the invention may be formed from any suitable materials, such as polymeric materials, ceramic and metals. Commonly employed materials include, but are not limited to, stainless steel, tempered blue steel, blackened corrosion resistant spring steel, and so forth.

The blades may optionally comprise a coating such as those applied to reduce the coefficient of friction between adjacent blade surfaces, and between any other surfaces the blades 20 may contact, such as an article 70. Examples of such materials include fluoropolymers. A specific example is polytetrafluoroethylene.

Various embodiments of the device 10 may be provided with various drive devices to accomplish rotation of a rotatable collar 28 with respect to the mount 34. FIGS. 1 and 2 show the rotatable collar 28 including an actuation lever 32 which may be used to manually rotate the collar 28. Rotation of the collar 28 may also be accomplished using any means known in the art including manual or automatic actuation. Actuation or drive devices may include, for example, motors and gear systems including stepping motors and spline gears, ball gears and/or lead screws; frictional methods such as rubber strips or belts; magnets with linear induction motors which incorporate bearings for smooth rotation; pneumatic screws; air cylinders; hydraulic cylinders; solenoids or any combination thereof. A drive device may further include linear motors available from Anorad Navigation, such as the LE Vacuum Compatible Linear Motor and PCLM Piezo Motor models; linear motor tables available from Parker Automation, such as the LXR series tables; and walking motor technology, such as PiezoLEGS motors available from PiezoMotor Uppsala AB, Sylveniusgatan 5D SE-754 50 Uppsala, Sweden. PiezoLEGS motors are available is sizes as small as 1 mm in width. Automatic drive devices may be computer controlled. Various embodiments of a drive device may be in communication with an actuation lever 32 or any other part of the collar 28. In some embodiments, a drive device may be in communication with a mount 34, and may rotate the mount 34 with respect to the collar 28 as the collar 28 may be fixed in position.

Figure 13:
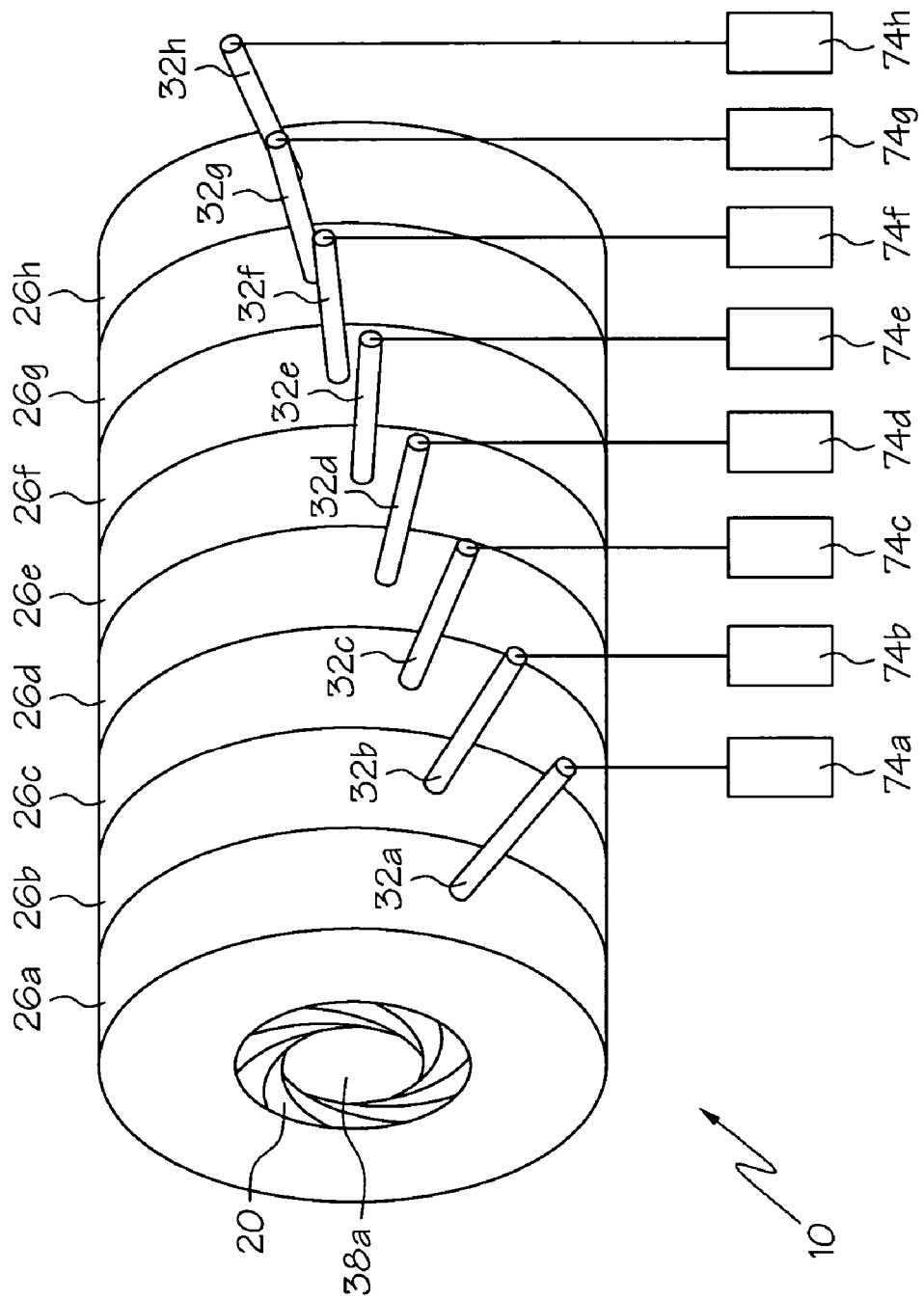
FIG. 13 shows an embodiment of the invention having multiple crimping sections.

FIG. 13 shows another embodiment of an inventive crimping device 10 which may include multiple crimping sections 26a–26h. Each crimping section 26 may include a mount, a collar and a plurality of blades 20 arranged to form an aperture 38 as previously described herein. The size of the aperture 38 may be adjusted by rotating the collar with respect to the mount. The aperture 38 of each crimping section 26 may be adjusted independently from all other crimping sections 26. The multiple crimping sections 26 may be arranged such that the center or zero point of each aperture 38 lies along a common axis, which may be the central longitudinal axis of the device 10.

Each crimping section 26 may include an independent drive device 74 arranged to adjust the size of the aperture 38. A drive device 74 may be in communication with the collar of a crimping section 26 and may rotate the collar with respect to the mount of the crimping section 26.

Embodiments of the device 10 having multiple crimping sections 26 may be used to crimp or otherwise load or bias a medical device. Each crimping section 26 may load a portion of a medical device. A stepped reduction in size may be achieved by placing a stent or similar medical device in a device 10 having multiple crimping sections 26 sequentially arranged, and independently reducing each aperture 38 to a desired size. For example, a medical device may be crimped to a tapered shape, or to have tapered end portions. Further, bifurcated stents or other medical devices having multiple sections of varying diameter may be crimped using embodiments of the inventive device 10 having multiple crimping sections 26.

Figure 14:
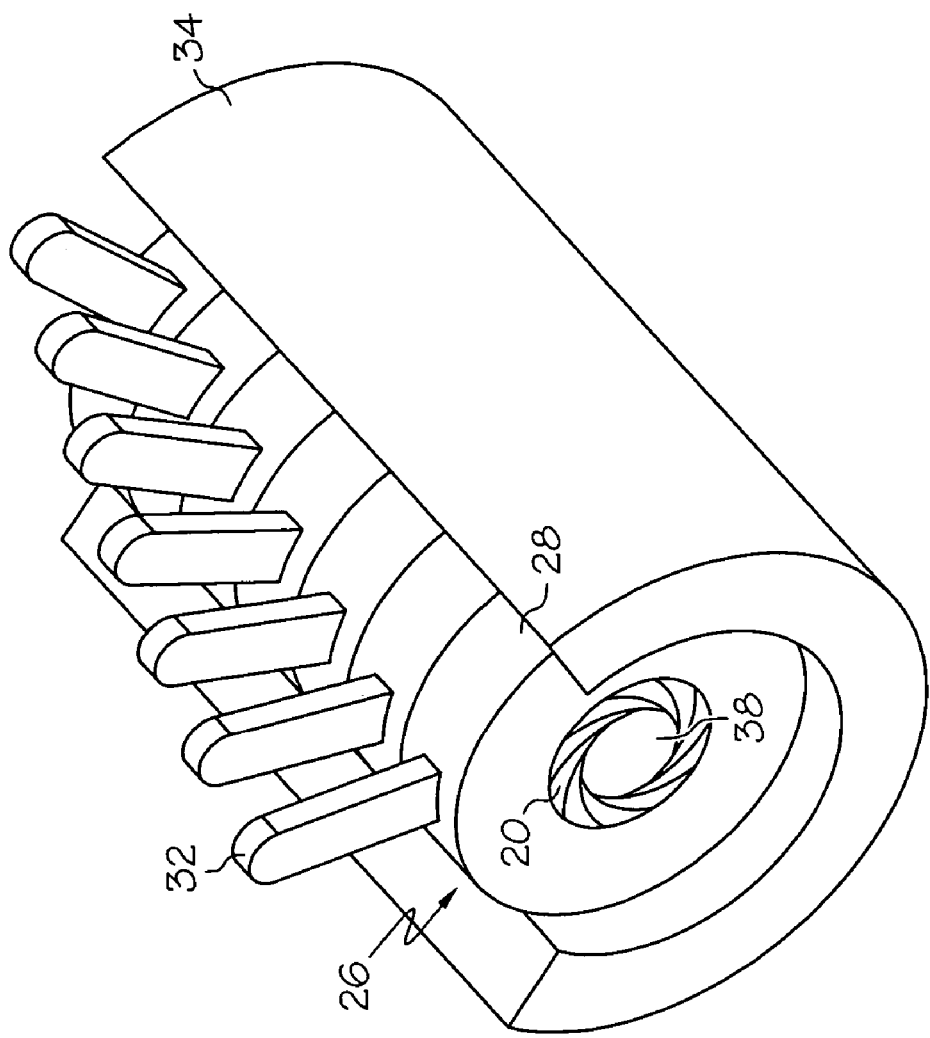
FIG. 14 shows another embodiment of the invention having multiple crimping sections.

FIG. 14 shows another embodiment of an inventive crimping device 10 which may have multiple crimping sections 26. Each crimping section 26 may include a collar 28 and a plurality of blades 20 arranged to form an aperture 38 as previously described herein. A single mount 34 may be used. Desirably, for each crimping section 26, the single mount 34 may include a portion arranged to receive a plurality of blades 20. The mount 34 may further be arranged to receive a collar 28 for each crimping section 26. The size of the aperture 38 of a crimping section 26 may be adjusted by rotating the collar 28 of the crimping section 26 with respect to the mount 34. Each crimping section 26 may be independently adjustable.

As shown in FIG. 14, a collar 28 may include an actuation handle 32 which may be arranged to abut a portion of the mount 34 at first and second ends of rotational travel. For example, the actuation handle 32 may abut a first surface of the mount 34 when the aperture 38 is fully open, and may abut a second surface of the mount 34 when the aperture 38 is closed. Where multiple crimping sections are employed, the individual sections may also be operated simultaneously. The individual sections may be operated independently from one another, or the operation may be coupled.

Figure 15:
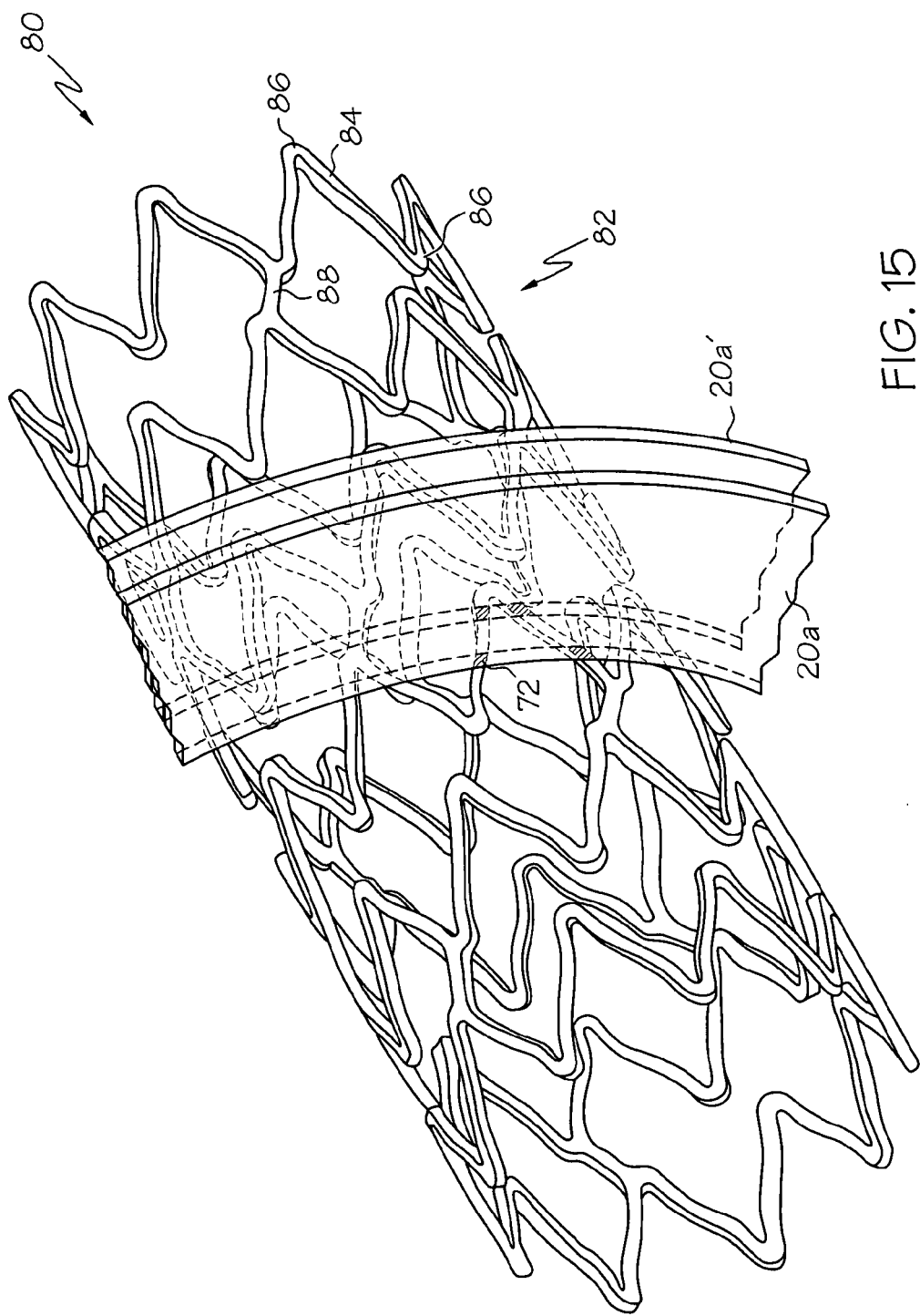
FIG. 15 shows a stent, a portion of blade from a first crimping section and a portion of a blade from a second crimping section.

FIG. 15 shows a portion of a stent 80, a first blade 20a and a second blade 20a'. The first blade 20a may be a blade 20 from a first crimping section forming a first aperture. The second blade 20a' may be a blade from a second crimping section forming a second aperture.

A stent 80 may comprise a framework having a plurality of cells. The framework of a stent 80 may include a plurality of serpentine bands 82. Each serpentine band 82 may include a plurality of struts 84. A strut 84 may be positioned adjacent to other struts 84 about the circumference of a serpentine band 82. Adjacent struts may be connected by a turn 86. Serpentine bands 82 may be positioned adjacent to one another along the longitudinal axis of the stent 80. Adjacent serpentine bands 82 may be connected by interconnecting elements 88. Each serpentine band 82 may have a length component, which may be measured in a direction parallel to the longitudinal axis of the stent 80. In some embodiments, a strut 84 may be parallel to the longitudinal axis of the stent 80 in an unexpanded state.

When a stent 80 is crimped using an inventive crimping device 10 having multiple crimping sections, at least two crimping sections may be arranged to apply a load to a serpentine band 82. The crimping device 10 may include at least two apertures within the length component of a serpentine band 82. The crimping device 10 may include at least two apertures along the length of a strut 84.

An inventive crimping device may be used to crimp a medical device directly about a catheter tube or to a catheter balloon which may be disposed about a catheter tube. When reference is made to crimping a medical device about a catheter, a balloon may be situated between the medical device and the catheter tube or the medical device may be crimped to a region of a catheter tube directly. The invention also contemplates crimping a stent in the absence of a catheter to reduce the stent in size.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the embodiments of the invention. Those skilled in the art may recognize other equivalents to the specific embodiment described herein which equivalents are intended to be encompassed by the claims attached hereto.

The invention claimed is:

1. A method of reducing the diameter of a stent in cross-section, the method comprising the steps of:
   1) providing an apparatus for applying an inward force to said stent, the apparatus comprising a first body portion, a second body portion and a plurality of movable blades arranged to form an aperture whose size may be varied, at least one blade pivotally attached to the first body portion and slidably engaged with the second body portion, wherein at least two blades overlap one another in a direction parallel to a central longitudinal axis of the aperture;
   2) disposing said stent within the aperture; and
   3) reducing the size of the aperture to apply an inward force to said stent, thereby reducing the diameter of the stent.

2. The method of claim 1, wherein the stent is self-expanding.

3. The method of claim 1, wherein the first body portion of the apparatus comprises a mount and the second body portion comprises a collar; each blade being pivotally attached to the mount and slidably engaged with the collar.

4. The method of claim 3, wherein the size of the aperture is reduced by rotating the collar with respect to the mount.

5. The method of claim 4, wherein the collar may be rotated with respect to the mount by a drive device.

6. The method of claim 1, the apparatus further comprising a second plurality of movable blades arranged to form a second aperture whose size may be varied, the method further comprising reducing the size of the second aperture to apply an inward force to said stent, thereby reducing the diameter of the stent.

7. The method of claim 6, the stent comprising at least one serpentine band having a length component in a direction parallel to a longitudinal axis of the stent, wherein the distance between the aperture and the second aperture is less than the length component of the serpentine band.

8. The method of claim 7, wherein the plurality of blades and the second plurality of blades are arranged to contact the same serpentine band.

9. The method of claim 1, wherein each blade comprises a contacting surface that may contact the stent, the contacting surface of at least one blade being curved.

10. The method of claim 1, wherein the blades have a thickness of about 0.025 mm to about 0.075 mm in a direction parallel to the central longitudinal axis of the aperture.

11. The method of claim 1, wherein the blades have a thickness of about 0.01 mm to about 2 mm in a direction parallel to the central longitudinal axis of the aperture.

12. A method of reducing the diameter of a medical device in cross-section, the method comprising the steps of:
   1) providing an apparatus for applying an inward force to said medical device, the apparatus comprising a mount, a collar and a plurality of movable blades arranged to form an aperture whose size may be varied by rotating the collar with respect to the mount, each blade being pivotally attached to the mount and slidably engaged with the collar, at least two blades overlapping in a direction parallel to a central longitudinal axis of the aperture, wherein the collar may be rotated with respect to the mount by a drive device comprising a lead screw, a ball screw, a solenoid, a movable rack actuator, a stepper motor or combination thereof;
   2) disposing a medical device within the aperture; and
   3) reducing the size of the aperture to apply an inward force to said medical device, thereby reducing the diameter of the medical device.

13. An apparatus for applying an inward force to a medical device, said apparatus comprising a plurality of coupled movable blades arranged to form an aperture whose size may be varied, the aperture having a central longitudinal axis, the blades including a first blade and a second blade, each blade comprising a contacting surface for contacting the medical device, the first blade overlapping the second blade in a direction parallel to the central longitudinal axis of the aperture, each blade having a thickness dimension in a direction parallel to the central longitudinal axis of the aperture, wherein a circumference of the aperture oriented orthogonal to the central longitudinal axis contacts the contacting surface of the first blade and the contacting surface of the second blade.

14. The apparatus of claim 13, wherein the contacting surface of each blade is curved.

15. The apparatus of claim 13, wherein the thickness dimension of each blade is 2 mm or less.

16. The apparatus of claim 13, each blade having a thickness dimension of about 0.025 mm to about 0.075 mm.

17. The apparatus of claim 13, wherein each blade is arranged to pivot about a pivot point.

18. The apparatus of claim 13 comprising 6 to 10 blades.

19. An apparatus for applying an inward force to a medical device, the apparatus comprising a first body portion, a second body portion and at least three coupled movable blades arranged to form an aperture whose size may be varied, each blade pivotally connected to the first body portion and slidably engaged with the second body portion, wherein at least two blades overlap one another in a direction parallel to a central longitudinal axis of the aperture.

20. The apparatus of claim 19, wherein each blade may overlap a portion of a first adjacent blade and each blade may be overlapped by a portion of a second adjacent blade in a direction parallel to the central longitudinal axis of the aperture.

21. The apparatus of claim 19, wherein each blade further comprises a contacting surface for contacting a medical device placed within the aperture, wherein the contacting surface of each blade is curved.

22. The apparatus of claim 19, comprising at least four blades.

23. The apparatus of claim 19, wherein the size of the aperture is controlled by the rotational orientation of the second body portion with respect to the first body portion.

24. The apparatus of claim 19, wherein each blade has a thickness dimension in a direction parallel to the central longitudinal axis of the aperture, wherein the thickness dimension of each blade is 2 mm or less.

25. The apparatus of claim 19 comprising 6 to 10 blades.

26. An apparatus for applying an inward force to a medical device, the apparatus comprising a mount, a rotatable collar and plurality of coupled movable blades arranged to form an aperture of variable size, each blade pivotally connected to the mount and slidably engaged with the rotatable collar, the size of the aperture being controlled by the rotational orientation of the rotatable collar with respect to the mount, wherein at least two blades overlap one another in a direction parallel to a central longitudinal axis of the aperture;

wherein each blade further comprises a pivot pin; the mount further comprises a plurality of apertures; and each aperture receives the pivot pin of a blade.

27. The apparatus of claim 26, wherein each blade further comprises a sliding pin; the second body portion further comprises a plurality of slots; and each slot receives the sliding pin of a blade.

28. The apparatus of claim 27, wherein the slots of the second body portion are oriented in a radial direction.

29. The apparatus of claim 28, wherein the sliding pin of a blade may translocate from a first position to a second position within a slot of the second body portion as the second body portion is rotated from a first rotational position to a second rotational position with respect to the first body portion.

30. An apparatus for applying an inward force to a medical device, the apparatus comprising a plurality of coupled movable blades arranged to form a first aperture of variable size, wherein at least two blades overlap one another in a direction parallel to a central longitudinal axis of the aperture;

the apparatus further comprising a second plurality of blades arranged to form a second aperture whose size may be varied, the second aperture adjustable independently from the first aperture.

31. The apparatus of claim 30, further comprising a third plurality of blades arranged to form a third aperture whose size may be varied, the third aperture being independently adjustable.

32. The apparatus of claim 30, further comprising a first drive device for controlling the size of the first aperture and a second drive device for controlling the size of the second aperture.

33. An apparatus for applying an inward force to a medical device, the apparatus comprising a mount, a rotatable collar and a plurality of coupled movable blades arranged to form an aperture of variable size, each blade pivotally connected to the mount and slidably engaged with the rotatable collar, wherein at least two blades overlap one another in a direction parallel to a central longitudinal axis of the aperture;

wherein the mount, the rotatable collar and the plurality of blades comprise a first crimping section; the apparatus further comprising a second crimping section, the second crimping section comprising a second rotatable collar and a second plurality of blades arranged to form a second aperture, each crimping section being independently adjustable.

34. The apparatus of claim 33, wherein the first aperture and the second aperture are arranged about a similar central longitudinal axis.

35. An apparatus for applying an inward force to a medical device, said apparatus comprising a mount, a rotatable collar and a plurality of coupled movable blades arranged to form an aperture whose size may be varied by rotating the collar with respect to the mount; each blade being pivotally attached to the mount and slidably engaged with the collar; each blade having a thickness dimension of 2 mm or less in a direction parallel to a central longitudinal axis of the aperture; wherein at least two blades overlap one another in a direction parallel to the central longitudinal axis of the aperture.

\* \* \* \* \*